(12) United States Patent
Raman et al.

(10) Patent No.: US 10,378,994 B2
(45) Date of Patent: Aug. 13, 2019

(54) WIRELESS VIBRATION MONITORING OF MOVABLE ENGINE PARTS

(71) Applicant: AI ALPINE US BIDCO INC., Wilmington, DE (US)

(72) Inventors: Venkatesh Raman, Bangalore (IN); Pavan Chakravarthy Nandigama, Bangalore (IN)

(73) Assignee: AI ALPINE US BIDCO INC., Wilmington, DE (US)

( * ) Notice: Subject to any disclaimer, the term of this patent is extended or adjusted under 35 U.S.C. 154(b) by 455 days.

(21) Appl. No.: 14/639,704

(22) Filed: Mar. 5, 2015

(65) Prior Publication Data

US 2016/0258836 A1 Sep. 8, 2016

(51) Int. Cl.
*G01M 5/00* (2006.01)
*G01M 15/14* (2006.01)
(Continued)

(52) U.S. Cl.
CPC ........ *G01M 5/0066* (2013.01); *G01M 13/028* (2013.01); *G01M 15/14* (2013.01);
(Continued)

(58) Field of Classification Search
CPC .... G01M 5/0066; G01M 15/14; G01N 29/04; G01N 29/44; G01N 29/2437; G01N 2291/269
See application file for complete search history.

(56) References Cited

U.S. PATENT DOCUMENTS

| | | | | | |
|---|---|---|---|---|---|
| 4,317,371 | A | * | 3/1982 | Wolfinger | ................ G01H 1/10 702/140 |
| 4,831,365 | A | * | 5/1989 | Thomas | ............. G05B 19/4065 340/680 |

(Continued)

FOREIGN PATENT DOCUMENTS

| | | | |
|---|---|---|---|
| CN | 203350983 U | * | 12/2013 |
| CN | 203366063 U |   | 12/2013 |

(Continued)

OTHER PUBLICATIONS

Parkash et al, Optimizing the Design of Connecting Rod under Static and Fatigue Loading, International Journal of Research in Management, Science & Technology (E-ISSN: 2321-3264) vol. 1; No. 1, Jun. 2013.*

(Continued)

*Primary Examiner* — Justin Seo
*Assistant Examiner* — David L Singer
(74) *Attorney, Agent, or Firm* — Fletcher Yoder, P.C.

(57) ABSTRACT

Condition based engine parts (e.g., movable engine parts) monitoring is disclosed. The techniques may enable detecting cracks present in engine parts while the engine is operational. In one embodiment, a system includes a wireless sensor configured to be disposed on a movable part internal to a machine and communicate wirelessly and a controller that includes a processor. The processor may be configured to initiate communication with the wireless sensor by receiving a wireless signal indicative of a frequency of vibration of the internal movable part from the wireless sensor, to obtain an acceptable threshold range of vibrations for the internal movable part from one or more data sources, to determine whether the frequency of vibration is within the acceptable threshold range of vibrations for the internal (Continued)

movable part, and to initiate preventative actions when the frequency is not within the acceptable threshold range.

34 Claims, 4 Drawing Sheets

(51) Int. Cl.
    *G01N 29/04*     (2006.01)
    *G01N 29/24*     (2006.01)
    *G01N 29/44*     (2006.01)
    *G01M 13/028*     (2019.01)

(52) U.S. Cl.
    CPC .......... *G01N 29/04* (2013.01); *G01N 29/2437* (2013.01); *G01N 29/44* (2013.01); *G01N 2291/269* (2013.01)

(56) References Cited

U.S. PATENT DOCUMENTS

| | | | | |
|---|---|---|---|---|
| 5,115,672 A * | 5/1992 | McShane | G01F 1/7082 | 137/554 |
| 5,319,296 A * | 6/1994 | Patel | G05B 19/4062 | 244/227 |
| 5,549,137 A * | 8/1996 | Lenz | G05D 7/005 | 137/486 |
| 5,602,757 A * | 2/1997 | Haseley | F04C 28/28 | 340/635 |
| 6,024,324 A * | 2/2000 | Maino | G01H 1/003 | 180/337 |
| 6,321,602 B1 * | 11/2001 | Ben-Romdhane | F16C 19/52 | 340/679 |
| 6,556,939 B1 * | 4/2003 | Wegerich | G01D 3/08 | 702/127 |
| 6,601,005 B1 * | 7/2003 | Eryurek | G01K 15/00 | 374/E15.001 |
| 6,756,908 B2 | 6/2004 | Gass et al. | | |
| 7,484,416 B1 * | 2/2009 | Klosinski | G01L 9/0072 | 714/25 |
| 7,696,893 B2 | 4/2010 | Cairo et al. | | |
| 8,568,099 B2 * | 10/2013 | Sabannavar | G01M 13/028 | 416/170 R |
| 9,528,629 B2 * | 12/2016 | Anderson | G05B 23/0235 | |
| 2003/0089177 A1 * | 5/2003 | Luthje | C23C 30/00 | 73/760 |
| 2005/0072239 A1 * | 4/2005 | Longsdorf | G05B 23/027 | 73/649 |
| 2005/0118703 A1 * | 6/2005 | Su | C12M 41/48 | 435/286.1 |
| 2005/0271499 A1 * | 12/2005 | Loy | F01D 11/025 | 415/1 |
| 2005/0273218 A1 * | 12/2005 | Breed | B60C 11/24 | 701/2 |
| 2006/0100797 A1 * | 5/2006 | Poorman | G01H 1/00 | 702/56 |
| 2006/0136110 A1 * | 6/2006 | Casey | B60G 17/0195 | 701/50 |
| 2006/0238332 A1 * | 10/2006 | Carle | G08C 17/00 | 340/539.1 |
| 2006/0265106 A1 * | 11/2006 | Giles | A01B 79/005 | 700/283 |
| 2007/0129207 A1 * | 6/2007 | Kanamori | H02K 11/24 | 475/331 |
| 2007/0229248 A1 * | 10/2007 | Mott | G01H 1/16 | 340/522 |
| 2008/0092520 A1 * | 4/2008 | Brown | H04Q 9/00 | 60/226.1 |
| 2008/0243287 A1 * | 10/2008 | Potdar | F01D 17/145 | 700/108 |
| 2008/0312756 A1 * | 12/2008 | Grichnik | G05B 19/0423 | 700/29 |
| 2009/0092491 A1 * | 4/2009 | Cairo | F04D 27/001 | 416/61 |
| 2009/0229367 A1 * | 9/2009 | Boetius | G01H 1/003 | 73/660 |
| 2009/0250859 A1 * | 10/2009 | Okumura | B23D 31/003 | 269/74 |
| 2010/0082276 A1 * | 4/2010 | Becker | F03D 7/0276 | 702/56 |
| 2010/0198534 A1 * | 8/2010 | Hala | G01H 1/003 | 702/56 |
| 2010/0250170 A1 * | 9/2010 | Kalinin | B60C 23/0408 | 702/77 |
| 2011/0133949 A1 * | 6/2011 | Subramanian | F23R 3/00 | 340/870.28 |
| 2011/0248846 A1 * | 10/2011 | Belov | H04Q 9/00 | 340/539.1 |
| 2012/0053851 A1 * | 3/2012 | Baller | F03D 1/0658 | 702/34 |
| 2012/0068822 A1 * | 3/2012 | Sheikman | G01S 5/00 | 340/7.2 |
| 2012/0136627 A1 * | 5/2012 | Jensen | G05B 23/0235 | 702/182 |
| 2012/0145117 A1 * | 6/2012 | Wilkins | F16C 7/04 | 123/197.3 |
| 2012/0156034 A1 * | 6/2012 | Sabannavar | G01M 13/028 | 416/1 |
| 2012/0227538 A1 * | 9/2012 | Dodman | F16C 7/023 | 74/579 E |
| 2012/0256761 A1 * | 10/2012 | Mitchell | G01D 3/036 | 340/870.02 |
| 2013/0096848 A1 * | 4/2013 | Hatch | G01M 13/045 | 702/39 |
| 2013/0283942 A1 * | 10/2013 | Bouillot | B64D 45/0005 | 74/89 |
| 2013/0299000 A1 * | 11/2013 | Gillette, II | B67D 3/0003 | 137/2 |
| 2013/0304351 A1 * | 11/2013 | Gillette, II | G01N 33/0009 | 701/101 |
| 2013/0332010 A1 * | 12/2013 | Ziarno | G05B 23/0213 | 701/3 |
| 2013/0332011 A1 * | 12/2013 | Ziarno | G05B 23/0213 | 701/3 |
| 2014/0005960 A1 * | 1/2014 | Anderson | G05B 23/0235 | 702/56 |
| 2014/0046494 A1 * | 2/2014 | McAlister | G06F 1/26 | 700/287 |
| 2014/0174400 A1 * | 6/2014 | Dunbar | F16C 7/023 | 123/197.3 |
| 2014/0180605 A1 * | 6/2014 | Richerson | G01M 15/06 | 702/33 |
| 2015/0184614 A1 * | 7/2015 | Langenfeld | F16J 3/06 | 60/517 |
| 2015/0211951 A1 * | 7/2015 | Willis | F02C 6/12 | 73/487 |
| 2015/0330869 A1 * | 11/2015 | Ziarno | G01M 15/14 | 701/34.4 |

FOREIGN PATENT DOCUMENTS

| | | |
|---|---|---|
| CN | 103502638 A | 1/2014 |
| EP | 0087813 B1 | 12/1986 |
| EP | 2 345 878 A2 | 7/2011 |
| JP | 2013083489 A * | 5/2013 |
| KR | 101065485 B1 * | 9/2011 |
| WO | 9527183 A1 | 10/1995 |
| WO | 03/006935 A1 | 1/2003 |

OTHER PUBLICATIONS

Doshi et al, Analysis of Connecting Rod Using Analytical and Finite Element Method, International Journal of Modern Engineering Research (IJMER) vol. 3, Issue.1, Jan.-Feb. 2013 pp. 65-68.*
Miller, Balancing the Crankshaft to the Piston/Connecting Rod Assembly for a Single Cylinder Engine, May 29, 2008.*
Wen et al, Finite Element Analysis of Vehicle Engine Connection Rod under Mechanical load, Advanced Materials Research Online: Aug. 16, 2011 ISSN: 1662-8985, vols. 314-316, pp. 653-656.*

(56) References Cited

OTHER PUBLICATIONS

Ramani et al, FE-Analysis of Connecting Rod of I.C.Engine by Using Ansys for Material Optimization, Int. Journal of Engineering Research and Applications ISSN : 2248-9622, vol. 4, Issue 3( Version 1), Mar. 2014, pp. 216-220.*
Det Norske Veritas, Unbalanced engine forces and vibration on board ships, 1997.*
Rao et al, Vibration Analysis of Two Wheeler Connecting Rod, International Journal of Science and Research (IJSR) vol. 3 Issue 6, Jun. 2014.*
Caruso et al, Connecting Rod Manual (Year: 2006).*
Barelli et al, Diagnosis of internal combustion engine through vibration and acoustic pressure non-intrusive measurements, Applied Thermal Engineering 29 (2009) 1707-1713 (Year: 2009).*
Caterpillar, G3500 Cat® Engines for Gas Applications, (Year: 2008).*
Caterpillar, Gas Generator Set G3516, (Year: 1997).*
Somashekar et al, Vibration Signature Analysis of IC Engine, International Journal of Innovative Research & Development (Year: 2013).*
Machine Translation of JP2013083489 (Year: 2018).*
European Search Report and Opinion issued in connection with corresponding EP Application No. 16157724.2 dated Jul. 1, 2016.
Beech Marks, Fatigue Failure, and High Compression Pistons, Retrieved from the Internet URL: http://mechanicsupport.blogspot.in/2011/02/beech-marks-fatigue-failure-and-high.html, on Apr. 19, 2018, pp. 1-2 (Feb. 17, 2011).
Office Action issued in connection with corresponding EP Application No. 16157724.2 dated Feb. 26, 2018.
Chinese Office Action for CN Application No. 201610123829.X dated Jun. 13, 2019; 10 pgs.

* cited by examiner

WIRELESS VIBRATION MONITORING OF MOVABLE ENGINE PARTS

BACKGROUND

The subject matter disclosed herein relates to engine parts (e.g., movable engine parts) monitoring and, more specifically, to techniques to detect conditions, such as cracks, on operational parts of engines in real-time.

Moving parts in engines that develop one or more cracks may lead to an undesirable maintenance event of the engines if the crack goes undetected. For example, an undetected cracked turbine blade in a gas turbine engine may release from its holding disk, thereby potentially causing an undesirable maintenance event. In addition, an undetected cracked connecting rod in a reciprocating internal combustion engine could break apart and be released from its cap, thereby potentially causing an undesirable maintenance event.

Oftentimes, to inhibit the potential consequences of operating an engine with cracked movable parts, operators use schedule based monitoring of movable parts included in engines. Schedule based monitoring may refer to replacing a movable part after a certain time period regardless of the movable part's condition. That is, after a certain amount of use, such as 6 months, a year, and so forth, some movable parts are replaced without ascertaining the condition of the movable part. This may waste resources by replacing a movable part that may have a substantial remaining useful life. Also, schedule based monitoring may not catch a movable part that is cracked in time before it causes an undesirable maintenance event. In scenarios where condition based monitoring is used, sensors may be placed on movable parts of an engine to communicate data to a controller that monitors various characteristics of the movable parts. However, the sensors typically connected via wires to the controller. The wires on sensors attached to moving parts may become tangled as the engine operates, which may lead to the wires disconnecting from the sensor and/or the controller. Thus, it is desirable to enhance condition based monitoring of internal movable parts of engines while the engines are in operation to detect cracks before they develop further.

BRIEF DESCRIPTION

Certain embodiments commensurate in scope with the present disclosure are summarized below. These embodiments are not intended to limit the scope of the claimed disclosure, but rather these embodiments are intended only to provide a brief summary of possible forms of the disclosure. Indeed, the disclosure may encompass a variety of forms that may be similar to or different from the embodiments set forth below.

In one embodiment, a system includes a wireless sensor configured to be disposed on a movable part internal to a machine and communicate wirelessly and a controller including a processor. The processor configured to initiate communication with the wireless sensor by receiving a wireless signal indicative of a frequency of vibration of the internal movable part from the wireless sensor, to obtain an acceptable threshold range of vibrations for the internal movable part from one or more data sources, to determine whether the frequency of vibration is within the acceptable threshold range of vibrations for the internal movable part, and to initiate preventative actions when the frequency is not within the acceptable threshold range.

In another embodiment, a device includes a processor. The processor is configured to initiate communication with a wireless sensor disposed on a movable part internal to a machine by receiving a wireless signal indicative of a frequency of vibration of the internal movable part, to obtain an acceptable threshold range of vibrations for the internal movable part from one or more data sources, to determine whether the frequency of vibration is within the acceptable threshold range of vibrations for the internal movable part, and to initiate preventative actions when the frequency is not within the acceptable threshold range.

In another embodiment, a non-transitory, computer-readable medium stores computer instructions. The instructions, when executed by a processor, are configured to initiate communication with a wireless sensor disposed on a movable part internal to a machine by receiving a wireless signal from the wireless sensor, the wireless signal indicative of a frequency of vibration of the internal movable part, to obtain an acceptable threshold range of vibrations for the internal movable part from one or more data sources, to determine whether the frequency of vibration is within the acceptable threshold range of vibrations for the internal movable part, and to initiate preventative actions when the frequency is not within the acceptable threshold range.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
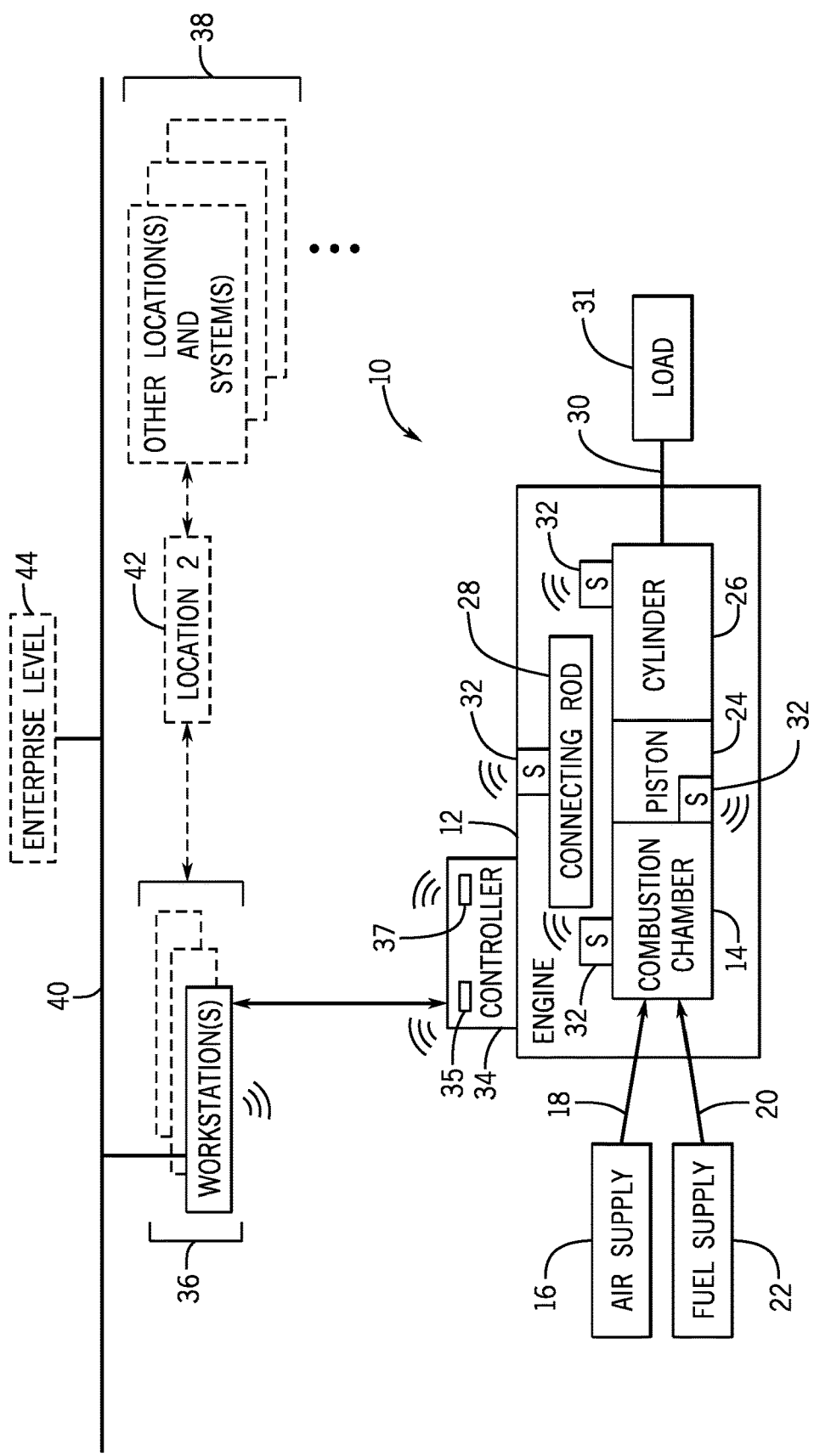
FIG. 1 is a block diagram of an embodiment of a reciprocating engine system using the disclosed condition based monitoring techniques.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Various components of an engine may experience degradation, including cracking, as a result of use. For example, components that may experience degradation include a connecting rod in a reciprocating internal combustion engine and a turbine blade in a gas turbine engine. The connecting rod and turbine blade may experience static and dynamic forces, thermal changes, as well as other stress factors, during operation. If the components are not properly maintained, or a crack goes undetected, the degradation factors may cause undesired maintenance events. Thus, it may be desirable to monitor certain characteristics of the movable parts to detect conditions, such as cracking, before the conditions worsen.

Accordingly, embodiments of the present disclosure relate to providing real time engine parts monitoring to detect an undesired maintenance condition and/or to predict when maintenance should be performed on the engine. In an embodiment, wireless based sensors (e.g., accelerometers) may be attached to internal movable parts of an engine to detect cracks on the internal movable parts while the engine is operational. The accelerometer may continuously or periodically monitor the frequency of the parts as they move and transmit the data wirelessly to a controller. The controller may determine whether the vibration frequency deviates from an acceptable threshold obtained from a knowledge database of vibration limits or if the frequency deviates from a baseline. If a deviation is detected, the controller may perform one or more preventative actions, such as shutdown the engine, send an alert to display on the controller's user interface screen (e.g., human-machine interface), send an alert to display on one or more remote workstations, or some combination thereof. In some embodiments, if a deviation is detected, one or more measurements may be obtained again to ensure that the deviation is consistent. If the subsequent check shows a consistent deviation, the controller may perform the one or more preventative actions noted above. Advantages of the disclosed condition based monitoring using wireless accelerometers may include saving time and cost on servicing the movable part with the detected crack, and the techniques may also inhibit undesirable maintenance events. Commercially, this may add value for an engine operator with potential for improved engine reliability.

Turning to the figures, FIG. 1 illustrates a block diagram of an embodiment of a reciprocating engine system 10 using the disclosed condition based monitoring techniques. The system 10 includes an engine 12 (e.g., a reciprocating internal combustion engine) having one or more combustion chambers 14 (e.g., 1, 2, 3, 4, 5, 6, 7, 8, 10, 12, 14, 16, 18, 20, or more combustion chambers 14). Exemplary engines 12 may include General Electric Company's Jenbacher Engines (e.g., Jenbacher Type 2, Type 3, Type 4, Type 6 or J920 FleXtra) or Waukesha Engines (e.g., Waukesha VGF, VHP, APG, 275GL), for example transportation engines. An air supply 16 is configured to provide a pressurized oxidant 18, such as air, oxygen, oxygen-enriched air, oxygen-reduced air, or any combination thereof, to each combustion chamber 14. The combustion chamber 14 is also configured to receive a fuel 20 (e.g., a liquid and/or gaseous fuel) from a fuel supply 22, and an air-fuel mixture ignites and combusts within each combustion chamber 14. As may be appreciated, the engine 12 may be a duel fuel engine which is configured to use a combination of liquid and gaseous fuel. In some embodiments, the pressurized oxidant 18 and fuel 20 may be supplied to and mixed in an intake manifold, which supplies the air-fuel mixture to the combustion chamber 14. Also, in some embodiments, a portion of the oxidant 18 and fuel 20 may be pre-mixed in a manifold for supply to the combustion chamber 14 (e.g., for pre-ignition) in addition to a separate supply of oxidant 18 and/or fuel 20 being directly supplied to the combustion chamber. The hot pressurized combustion gases cause a piston 24 adjacent to each combustion chamber 14 to move linearly within a cylinder 26 and convert pressure exerted by the gases into a rotating motion via a connecting rod 28 connecting the piston 24 to a crank, which causes a shaft 30 to rotate. The shaft 30 may be coupled to a load 31, which is powered via rotation of the shaft 30. For example, the load 31 may be any suitable device that may generate power via the rotational output of the system 10, such as an electrical generator. Additionally or alternatively, the load 31 may include a mechanical drive, compressor, pump, and the like. Once the available energy is translated into rotating the shaft 30, the remaining fuel 20 and/or oxidant 18 is vented and removed from the engine 12 as exhaust.

Various internal components of the engine 12 may include one or more attached sensors 32 (e.g., accelerometer, current sensor, thermal sensor) in wireless communication with a controller 34. The controller 34 may be an engine control unit (ECU) and may include one or more processors 35 configured to send a signal to a network interface to communicate with one or more workstations 36. Further, the controller 34 may include one or more memories 37 that store the computer instructions executed by the processors 35 to perform the techniques disclosed herein. As illustrated, the sensors 32 may be located on any part (e.g., movable part) internal to the engine 12, including the connecting rod 28, the combustion chamber 14, the piston 24, the cylinder 26, among others. The sensors 32 and the controller 34 may communicate using a standard network protocol, such as Bluetooth®, Dust Networks®, Z-wave®, WiFi, and ZigBee® via respective communication components. Other wireless communication technologies that may be used are infrared and radio. In some embodiments, Bluetooth® may be preferable for its short transmission range because the distances between the parts including the sensors and the controller 34 may generally be between 1 and 5 meters. Also, using Bluetooth® as the communication protocol may reduce the amount of power consumed by each transmission, which may be beneficial when using sensors 32 with an internal power source (e.g., batteries). It should be appreciated that using a wireless communication protocol to relay data from the sensors 32 to the controller 34 may enable the sensors to be placed on components internal to the engine 12 where it would be difficult to run wires. Further, using Bluetooth® based sensors 32 enables placing the sensors 32 on parts of the engine 12 that may move and/or rotate, such as the connecting rod 28. For example, if wires were connected to the sensors on the movable parts, the wires may become tangled and disconnect from the sensor and/or the controller.

In some embodiments, when the controller 34 is activated, the controller 34 may perform an initialization and handshake process with each sensor 32. For example, the controller 34 may contact each sensor 32 individually and transmit a command instruction for the sensor 32 to activate. Upon sensor 32 activation, the controller 34 may perform a pairing and authentication handshake process with the sensors 32. Once the controller 34 and the sensors 32 are wirelessly connected and able to communicate data, the controller 34 may request certain information from the sensors 32 or the sensors 32 may transmit certain information by default. The information may relate to the type of sensor 32 (e.g., accelerometer, thermal, current), the power source used by the sensor 32, the type of data the sensor 32 transmits (e.g., kind, size), the transmission schedule, the parts to which the sensors 32 are attached, and the like.

As will be described in detail below, in one embodiment, the sensors 32 may be accelerometers that measure the frequency of vibrations of moving parts in the engine 12 and transmit the frequency signal continuously or on a periodic basis to the controller 34 to detect undesired conditions of movable parts, such as cracks. The controller 34 may compare the received frequency of vibration signal for the particular movable part to a knowledge database that includes the natural frequency or acceptable range of frequencies for the movable part as provided in a specification or determined during testing of the movable part. If the frequency exceeds the acceptable limit in the database, then the controller 34 may take one or more preventative actions, such as deactivating the engine 12, sending an alert to display on a user interface screen included with the controller, sending an alert to display at the workstations 36, or some combination thereof. If the frequency is within the acceptable threshold range, then the controller 34 may permit the continued operation of the engine 12 and continue to monitor the condition of the movable part.

The controller 34 may be in wireless or wired communication (e.g. Ethernet) with the workstations 36 and capable of transmitting data over a long range to the workstations 36. A workstation 36 may be located in the same site, plant, factory, etc. ("location 1") as the system 10. However, the controller 34 may be capable of communicating with workstations 36 external to location 1 and other locations and systems 38 over a network 40 (e.g., Internet). The controller 34 may wirelessly communicate with workstations 36, other components located in "location 2" 42, and/or other locations and systems 38. The various workstations 36, locations (42), and other locations and systems 38 may all communicate with one another and data related to each system may be stored at an enterprise level 44 via network 40. For example, at the enterprise level 44, an entity may maintain engines running at any number of locations by monitoring the data received from the controller 34, the workstations 36, and so forth.

Figure 2:
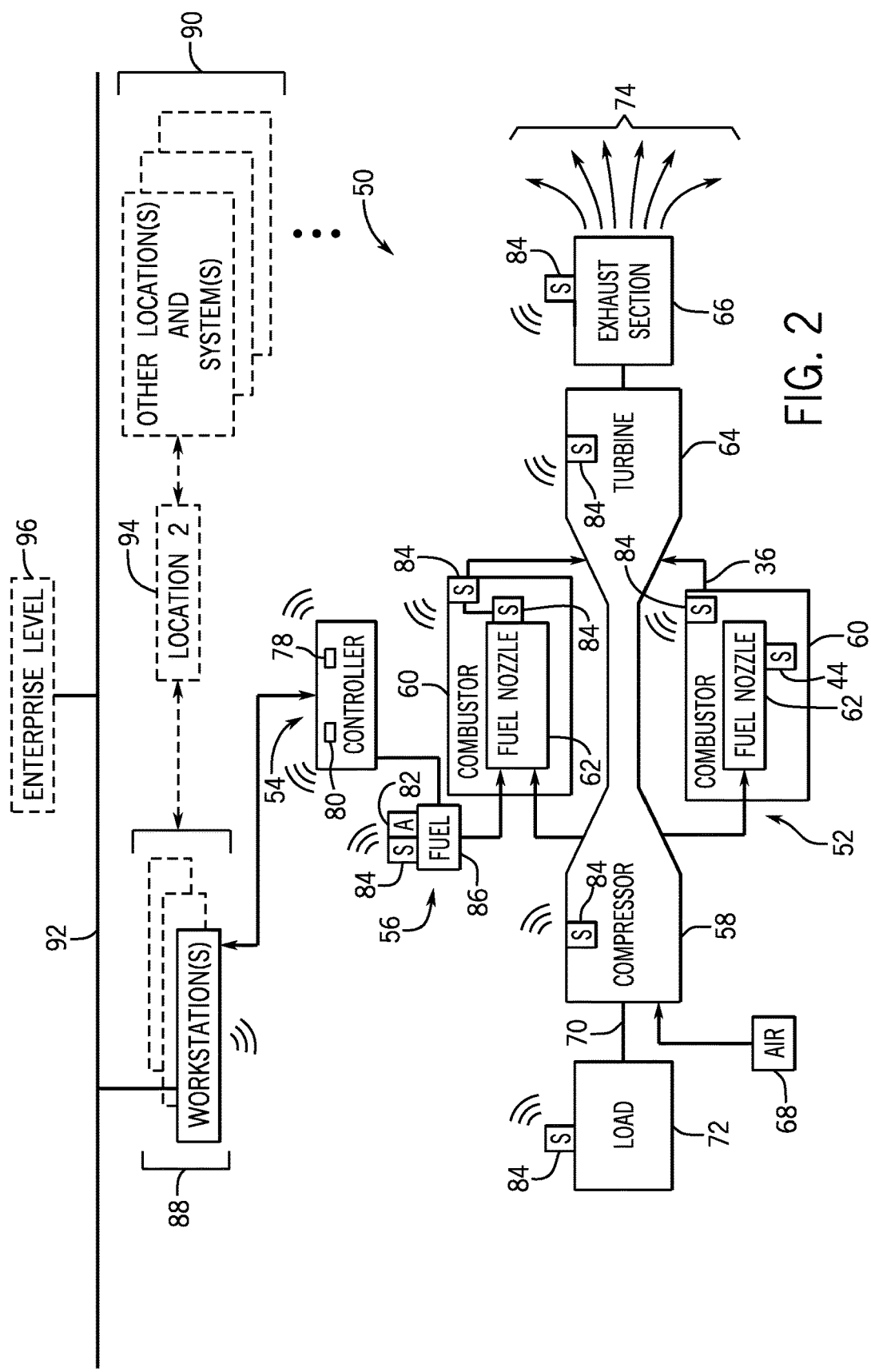
FIG. 2 is a block diagram of an embodiment of a gas turbine engine system using the disclosed condition based monitoring techniques.

FIG. 2 is a block diagram of an embodiment of a gas turbine engine system 50 using the disclosed condition based monitoring techniques. In certain embodiments, the gas turbine engine system 50 may include a gas turbine 52, a controller 54 (e.g., engine control unit), and a fuel supply system 56. As illustrated, the gas turbine 52 may include a compressor 58, combustion system 60, fuel nozzle 62, turbine 64, and exhaust section 66. During operation, the gas turbine 52 may intake gas (e.g., air) 68 into the compressor 58, which then compresses the air 68 and moves it to the combustion system 60 (e.g., a plurality of combustors). In the combustion system 60, the fuel nozzle 62 (or a plurality of fuel nozzles 62) injects fuel that mixes with the compressed air creating an air-fuel mixture. The air-fuel mixture may combust in the combustion system 60 to generate hot combustion gases, which flow downstream into the turbine 64 to drive one or more turbine 64 stages. For example, the combustion gases move through the turbine 64 to drive one or more stages of turbine 64 blades, which in turn drive rotation of shaft 70. The shaft 70 connects to a load 72, such as a generator that uses the torque of the shaft 70 to produce electricity. After passing through the turbine 64, the hot combustion gases may vent as exhaust gases 74 into a bottoming cycle system (e.g., HRSG), through the exhaust section 66.

In certain embodiments, the controller 54 may include a processor 78, a memory 80, a hardware interface (not shown) suitable for interfacing with the actuators 82 and the sensors 84, and a communication component (not shown) suitable for wirelessly communicating with the sensors 84. Accordingly, the controller 54 may be wirelessly communicatively coupled to sensors 84, via any suitable wireless technology (e.g., Bluetooth®), such that the controller 54 may receive data from the sensors 84 and send command instructions to the sensors 84. The memory 80 may contain computer instructions stored on a tangible, non-transitory computer-readable medium that perform the condition based monitoring (e.g., crack detection) techniques disclosed herein. As illustrated, the wireless sensors 84 may be attached to numerous components in the system 50, such as the fuel supply system 56, the combustion system 60, the fuel nozzle 62, the compressor 58 and internal components of the compressor (e.g., compressor blades), the turbine 64 and internal components of the turbine (e.g., turbine blades), the load 72, the exhaust section 66, and so forth.

In some embodiments, the sensors 84 may include accelerometers configured to transmit vibration parameter (e.g., vibration frequency, velocity, acceleration, or displacement) signals to the controller 54. For example, as described in detail below, a wireless based sensor 84 may be attached to a movable part internal to the casing of the turbine 64, such as a turbine blade, and the sensor 84 may transmit the frequency of the turbine blade as the turbine blade rotates during engine operation. In this way, the controller 54 may detect whether the frequency of the turbine blade exceeds an acceptable threshold during operation based on the sensor 84 data and determine that the blade may be cracked. As a result, the controller 54 may perform a preventative action, such as deactivating the engine 50, sending an alert to display on a user interface screen included with the controller, sending an alert to display at the workstations 88, or some combination thereof. As previously noted, using wireless based sensors 84 enables monitoring data specific to certain parts that may be inaccessible to wires and/or incompatible with wires, such as parts that are located internally to the engine and that move and/or rotate. Further, the disclosed techniques may enable detecting certain conditions while the system 50 is operational, which may inhibit the condition from worsening and potentially causing an undesirable maintenance event.

In addition, in response to the sensor 84 data, the processor 78 may execute instructions stored on the memory 80 to control components of the gas turbine system 50 (e.g., fuel system 56) via the actuators 82. The actuators 82 may include valves, pumps, positioners, inlet guide vanes, switches, and so on, useful in performing control actions. The sensors 84 may provide various data to the controller 54 including, for example, the amount of fuel 86 provided to the combustion system 62, the temperature of the fuel 86, the pressure ratio of the compressor 58, and the inlet temperature of the compressor 58.

Further, as described above with regards to the reciprocating engine system 10, the gas turbine engine system's controller 54 may be in wireless or wired communication (e.g. Ethernet) with one or more workstations 88 and capable of transmitting data over a long range to the workstations 88. A workstation 88 may be located in the same site, plant, factory, etc. ("location 1") as the system 50.

However, the controller 54 may be capable of communicating with workstations 88 external to location 1 and other locations and systems 90 over a network 92 (e.g., Internet). The controller 54 may wirelessly communicate with workstations 88, other components located in "location 2" 94, and/or other locations and systems 90. The various workstations 88, locations (94), and other locations and systems 90 may all communicate with one another and data related to each system may be stored at an enterprise level 96 via network 92. For example, at the enterprise level 96, an entity may maintain engines running at any number of locations by monitoring the data received from the controller 54, the workstations 88, and so forth.

Figure 3:
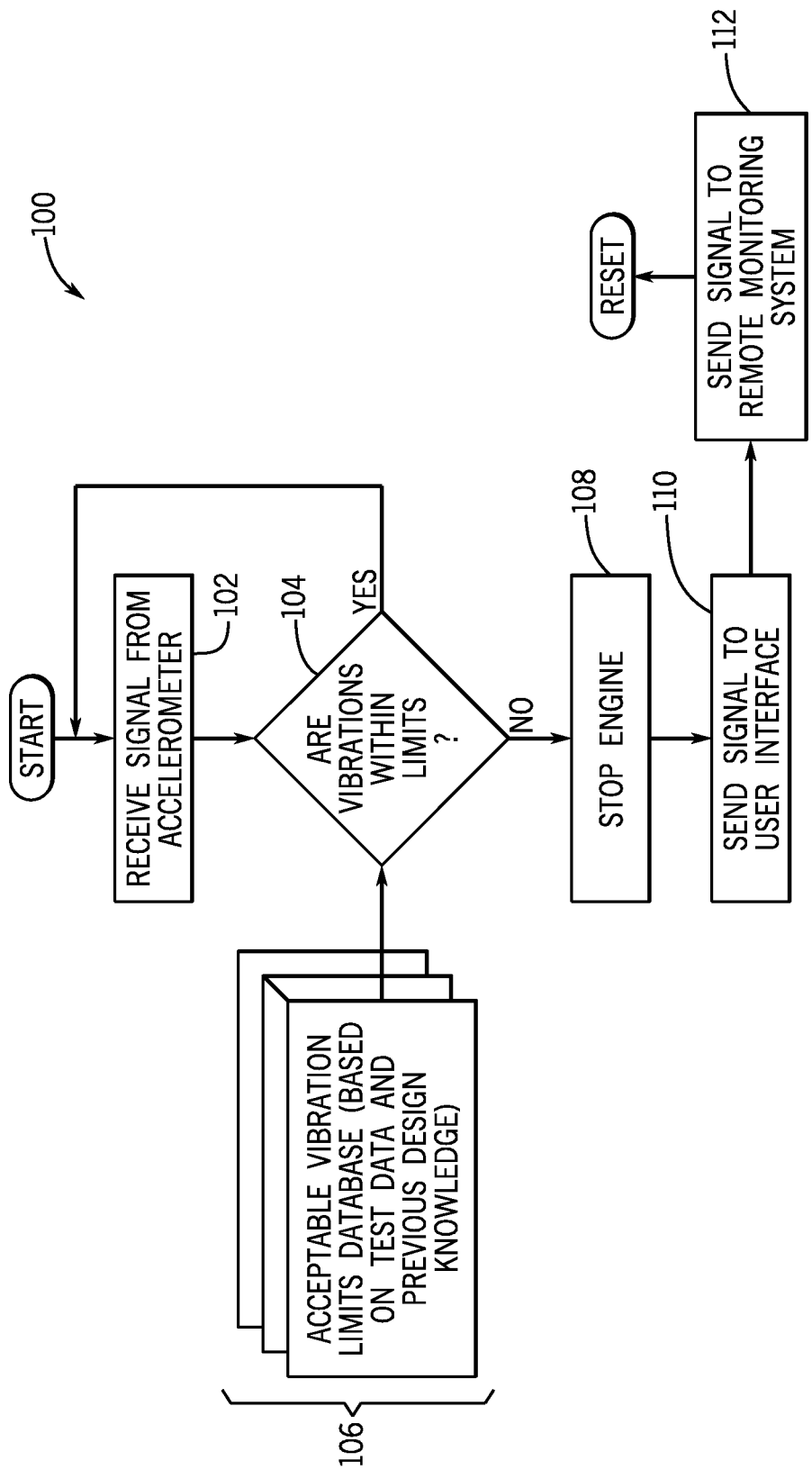
FIG. 3 is a flow diagram of an embodiment of a process suitable for detecting conditions (e.g., cracks) of components while an engine is operational in accordance with the present techniques.

FIG. 3 is a flow diagram of an embodiment of a process 100 suitable for detecting conditions (e.g., cracks) of components while an engine is operational in accordance with the present techniques. It should be noted that discussion of the process 100 below references elements from FIG. 1 but the discussion also applies to FIG. 2 where like elements perform like functionalities. The process 100 may be implemented as computer instructions stored on one or more tangible, non-transitory computer-readable medias (e.g., memories 37) and executable by one or more processors 35 included in the controller 34. The process 100 may include receiving a signal from an accelerometer (process block 102) and determining whether the vibration frequency is within certain limits (decision block 104) by comparing the received frequency against one or more databases of acceptable vibration limits (database 106). It should be noted that the accelerometer may be used as the sensor 32. If the vibration frequency is within the acceptable limits, then the process 100 may return to waiting to receive the next signal from the accelerometer 32 (process block 102). If the vibration frequency exceeds the acceptable vibration limit, then the controller 34 may execute command instructions to stop the engine (process block 108). Further, the controllers 34 may send an alert to display or trigger an alarm on the user interface (process block 110) and send a signal to one or more remote monitoring systems, such as workstations 36 (process block 112).

More specifically, regarding process block 102, in some embodiments, the accelerometer 32 may be configured to continuously transmit the frequency signal of the movable part to which it is attached to the communicably coupled controller 34. In other embodiments, the accelerometer 32 may be configured to transmit the frequency signal at a predetermined or configurable interval for a configurable amount of time. For example, the accelerometer 32 may transmit data every 10 seconds, 30 seconds, 1 minute, etc. for 1 hour, 2 hours, 3 hours, etc. In some embodiments, the controller 34 may request data based on a monitoring schedule or the controller 34 may demand faster transmissions if the controller 34 determines that the trend of the past readings are approaching the limits and the controller 34 determines that closely monitoring the movable part's status is desired. Also, in some embodiments, the controller 34 may obtain data related to the battery life of the wireless accelerometer 32. If the battery life of the accelerometer 32 is relatively low, then the controller 34 may command the accelerometer 32 to lengthen the interval between readouts to preserve the accelerometer's power.

Once the controller 34 receives the signal representing the frequency of the vibrations of the movable part being monitored (process block 102), the controller 34 will determine whether the vibration frequency is within an acceptable threshold range obtained from the acceptable vibration limits database 106. As previously noted, in some embodiments, there may be one or more acceptable vibration limits databases 106. For example, in one embodiment, the database 106 is located locally on the controller 34. In other embodiments, there may be several databases 106 that the controller 34 accesses to obtain the vibration limit data. That is, for example, a local database 106 may contain the vibration limits for certain proprietary movable parts (e.g., connecting rod) while another database 106 located at an external source may contain vibration limits for third party parts. It should be noted that any of the databases 106 may include the vibration limit data for numerous parts for numerous machines. Also, the database 106 data may be periodically updated by a software application stored on the controller's memory 37 that may call a web service to obtain current vibration limit data. In other embodiments, a third party service may push data updates to the database 106.

The data related to the acceptable vibrations limits may be obtained from test data about the acceptable vibrations of monitored movable parts, previous design knowledge (e.g., a specification), past observed frequencies associated with a crack, or some combination thereof. The data may be populated in the database 106 before the system 10 is activated. The acceptable vibration limits may refer to a threshold range of frequencies that are acceptable. Additionally, the database 106 may include a field for the normal vibration frequency of every part being monitored. To illustrate, the database 106 may indicate that the natural frequency of the connecting rod 28 may be 20 hertz (Hz). The acceptable range of frequencies as obtained by the specification or during testing of the connecting rod 28 may include 0-2 Hz deviation from 20 Hz. Any frequency outside of that range may indicate a crack is present. Cracked parts typically generate frequencies that vary from (e.g., are higher or lower than) the natural frequency of parts when the parts are whole. Thus, if the connecting rod 28 generates a vibration frequency of 25 Hz, then the controller 34 may determine that there is a crack present in the connecting rod 28. In other embodiments, the controller 34 may baseline the vibration frequency of the movable part at startup and monitor for a deviation from the baseline by a certain amount of Hz obtained from the database 106. In some embodiments, the baseline deviation may include measurements of the phase difference offset between the frequencies as captured.

In some embodiments, other parameters, such as angular velocity, acceleration, and displacement may be determined by the controller 34 based on signals received from one or more sensors. For example, a position sensor may be used in conjunction with the accelerometer 32 to transmit signals indicative of angular velocity. The controller 34 may receive the signals from the position sensor and the accelerometer 32 and perform a fast Fourier transform (FFT) to convert the signals to an angular velocity. Also, the frequency signals transmitted by the accelerometer may be used in FFTs by the controller 34 to determine an acceleration and displacement in Hz.

If the controller 34 determines that the movable part's frequency is outside of the acceptable threshold range, then the controller 34 may execute one or more preventative actions. The actions may include stopping the engine 12 (process block 108), sending a signal to the user interface provided by the controller 34 (process block 110), sending a signal to a remote monitoring system (e.g., workstations 36), or some combination thereof. Stopping the engine 12 (process block 108) may inhibit the crack from growing and causing the movable part to separate, which may lead to an undesired maintenance event. Sending a signal to the user interface (e.g., human-machine interface) (process block 110) of the controller 34 may include displaying the movable part for which the crack is detected and may alert an operator to replace the flagged part. Also, the signal may trigger an audio siren alarm at the controller 34. Further, sending a signal to a workstation 36 may include displaying the system 10 and the movable part (e.g., connecting rod 28) that is affected, which may enable an operator to stop other machines or systems that are affected by the engine 12 being stopped. Sending an alert to workstations 36 also enables the owner entity to keep track of system downtime, order replacement parts, schedule maintenance, and manage their fleet of systems more efficiently. In some embodiments, the controller 34 may automatically schedule a time to perform maintenance on the cracked movable part to reduce system downtime. After the preventative actions are taken by the controller 34, the process 100 may reset.

Figure 4:
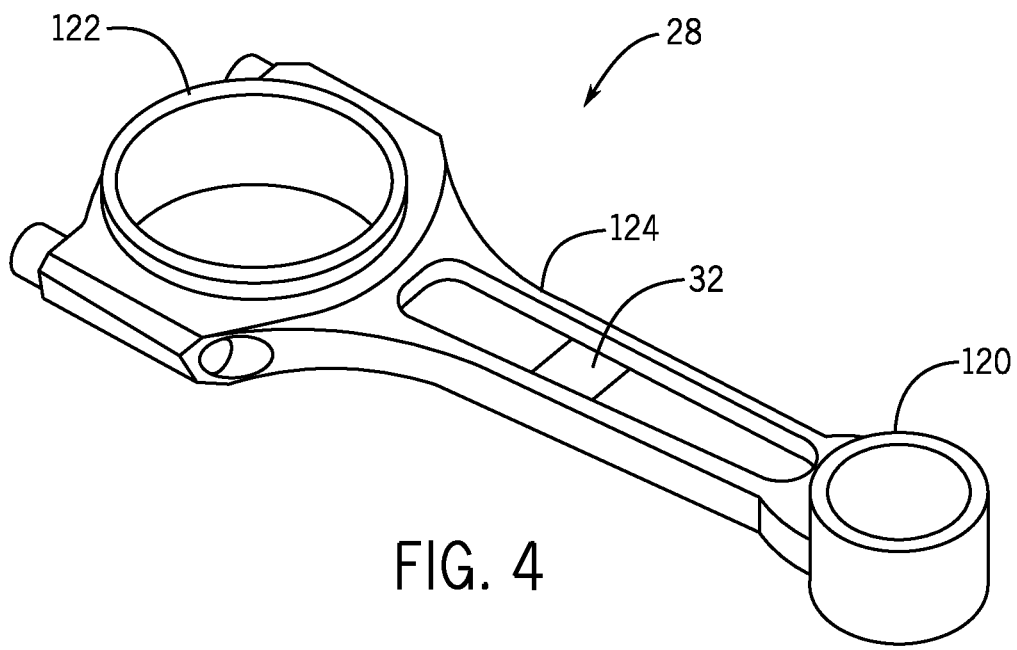
FIG. 4 illustrates a connecting rod including a sensor used in the reciprocating engine system of FIG. 1 in accordance with the present techniques.

FIG. 4 illustrates the connecting rod 28 including the sensor 32 used in the reciprocating engine system 10 of FIG. 1 in accordance with the present techniques. In the depicted embodiment, the sensor 32 may be an accelerometer used to measure vibration frequency. A proximate end 120 may connect to the piston 24 pin, which may be press fit into the connecting rod 28. The connecting rod's proximate end 120 may swivel in the piston 24. A distal end 122 of the connecting rod 28 may connect to a bearing journal of a crank throw. The proximate end 120 and the distal end 122 may be connected and separated by a shank 124. The connecting rod 28 may undergo significant stress during operation such as stretching and compressing. If any part of the connecting rod 28, such as the proximate end 120, the distal end 122, or the shank 124, cracks, the connecting rod 28 can break apart, thereby potentially causing an undesired maintenance event. As depicted, the accelerometer 32 may be attached to the center of the shank 124 to monitor the frequency of vibrations of the rod 28. As previously noted, vibration frequencies, frequency shift, or other parameters (e.g., velocity, acceleration, displacement) that exceed an acceptable threshold range may be indicative of a crack in the rod 28. It should be noted that the accelerometer 32 may be located anywhere along the rod 28 and is not limited to placement in the center of the shank 124. Further, using wireless accelerometers is desirable because the connecting rod 28 is located internally in the engine where it may be difficult to run wires and the connecting rod 28 may move rapidly in multiple directions during operation, which could cause any connected wires to become detached or tangled. That is, the connecting rod 28 may move arbitrarily (non-linearly) when the engine 12 is operational.

Figure 5:
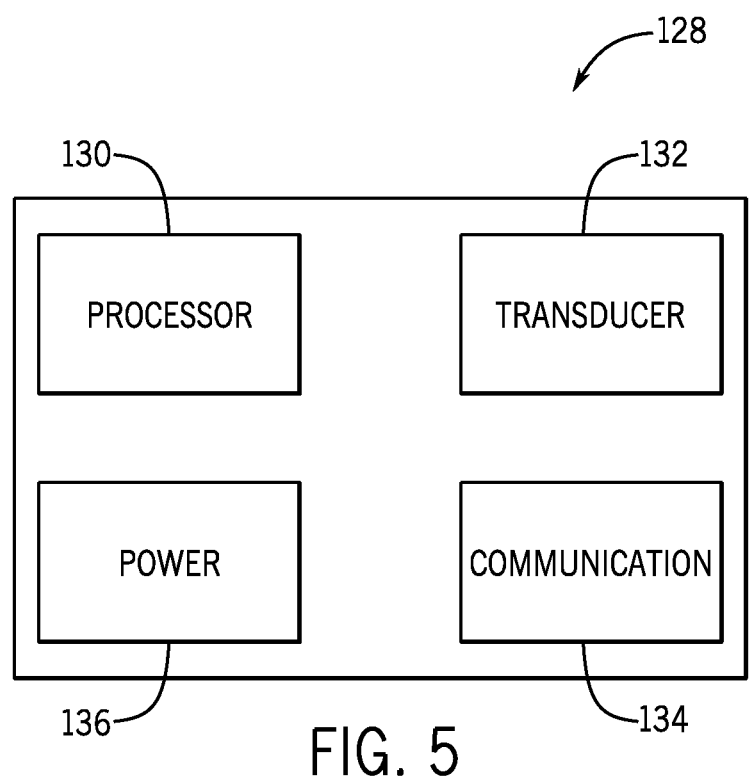
FIG. 5 is a block diagram of an embodiment of accelerometer that may be utilized in conjunction with the process of FIG. 3.

FIG. 5 is a block diagram of an embodiment of an accelerometer 128 that may be utilized in the process of FIG. 3. It should be noted that the accelerometer can be used as either or both sensor 32 and sensor 84. The accelerometer 128 may include a processor 130, a transducer 132, a communication component 134, and a power source 136. The accelerometer 128 may enable detecting and measuring the frequency of vibration of movable parts included in machinery, such as reciprocating engines and gas turbine engines. The transducer 132 may convert energy from one form to another. For example, the transducer 132 may include a piezoelectric material configured to convert vibration to an electric signal. That is, the frequency of vibration may be obtained by the piezoelectric material 132, which generates an electric signal indicative of the frequency when the piezoelectric material 132 is vibrated. When the piezoelectric material 132 experiences mechanical stress (e.g., vibrations), the positive and negative charge centers shift in the material 132, thereby causing an external electric signal to be generated. The processor 130 may receive the signal and cause the communication component 134 to transmit the signal indicative of frequency to the controller (e.g., 34 or 54) as discussed above. The communication component 134 may include a wireless card capable of communicating via any suitable wireless technology (e.g., Bluetooth®, WiFi, ZigBee®, radio, infrared), as discussed above. In some embodiments, the power source 136 may be a battery, capacitor, or other internal power source and may be capable of storing the charge generated by the piezoelectric material 132.

Technical effects of the disclosure may include detecting certain conditions, such as cracks, using condition based monitoring of movable parts internal to machinery via wireless based sensors and a control system. The techniques may include a controller receiving a signal from a wireless accelerometer indicative of the frequency of vibration of a monitored movable part. The controller may determine whether the frequency is within an acceptable threshold range and take certain preventative actions if not. Using the techniques disclosed herein may enable an entity to detect cracks and/or other potential faults prior to full separation, thereby inhibiting an undesired maintenance event. If a crack is detected, the engine may be stopped and the part may be quickly replaced, thereby reducing system downtime. Thus, the disclosed techniques may save time and expense on service to the machinery as well as prevent potential damage to the machinery caused by undetected faults. Also, monitoring the movable parts based on their conditions may enable leveraging the full life of the parts instead of replacing the parts without regard for their condition, as is done in schedule based monitoring.

This written description uses examples to disclose the techniques, including the best mode, and also to enable any person skilled in the art to practice the techniques, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   a wireless sensor disposed in a recess of a shank of a connecting rod internal to a reciprocating internal combustion engine and to communicate wirelessly; and
   a controller comprising a processor configured to:
   initiate communication with the wireless sensor by receiving a wireless signal indicative of a frequency of vibration of the connecting rod from the wireless sensor;
   obtain an acceptable threshold range of vibrations for the connecting rod from one or more data sources;
   determine whether the frequency of vibration is within the acceptable threshold range of vibrations for the connecting rod; and
   initiate preventative actions when the frequency is not within the acceptable threshold range, wherein the preventative actions comprise stopping operation of the reciprocating internal combustion engine.

2. The system of claim 1, wherein the processor is configured to wait for another wireless signal using a network interface, before initiating preventative actions, when the frequency is within the acceptable threshold range.

3. The system of claim 1, wherein the processor is configured to send an alert to display on a user interface screen of a control system, send the alert to a local or remote workstation to display, or some combination thereof, as the one or more preventative actions.

4. The system of claim 1, wherein the processor is configured to initiate communication with the wireless sensor by receiving a second wireless signal indicative of a second frequency of vibration of the connecting rod from the wireless sensor when the frequency is not within the acceptable threshold range prior to initiating preventative actions, determine whether the second frequency of vibration is within the acceptable threshold range of vibrations for the connecting rod, and to initiate preventative actions when the second frequency is not within the acceptable threshold range.

5. The system of claim 1, wherein the processor is configured to:
 initiate communication with the wireless sensor by receiving a wireless signal indicative of one or more angular velocity, acceleration, displacement, or some combination thereof, of the connecting rod from the wireless sensor;
 obtain an acceptable threshold range of angular velocity, acceleration, displacement, or some combination thereof, for the connecting rod from one or more data sources;
 determine whether the angular velocity, the acceleration, the displacement, or some combination thereof, is within the acceptable threshold range for the connecting rod; and
 initiate preventative actions when the angular velocity, the acceleration, the displacement, or some combination thereof, is not within the acceptable threshold range.

6. The system of claim 1, wherein the processor is configured to generate an indication that the connecting rod has cracked when the frequency of vibration exceeds the acceptable threshold range of vibration.

7. The system of claim 1, wherein the acceptable threshold range of vibrations for the connecting rod is based at least in part on a natural frequency of the connecting rod.

8. The system of claim 1, comprising an additional wireless sensor configured to be disposed on a piston internal to the reciprocating internal combustion engine and to output an additional wireless signal to the controller indicative of a frequency of vibration of the piston.

9. A system, comprising:
 a reciprocating combustion engine;
 a wireless sensor disposed in a recess of a shank of a connecting rod internal to the reciprocating combustion engine and to communicate wirelessly; and
 a controller comprising a processor configured to:
  initiate communication with the wireless sensor disposed in the recess of the shank of the connecting rod internal to the reciprocating combustion engine by receiving a wireless signal indicative of a frequency of vibration of the connecting rod;
  obtain an acceptable threshold range of vibrations for the connecting rod from one or more data sources;
  determine whether the frequency of vibration is within the acceptable threshold range of vibrations for the connecting rod; and
  initiate preventative actions when the frequency is not within the acceptable threshold range, wherein the preventative actions comprise stopping operation of the reciprocating combustion engine.

10. The system of claim 9, wherein the processor is configured to initiate waiting for another wireless signal using a network interface when the frequency is within the acceptable threshold range.

11. The system of claim 9, wherein the processor is configured to set a baseline value of the frequency of vibration when the wireless signal is initially received and to determine whether a phase of the frequency of vibration deviates from a phase of the baseline value for subsequently received wireless signals.

12. The system of claim 9, wherein obtaining the acceptable threshold range comprises accessing pre-stored test data, a design specification, or some combination thereof, related to the connecting rod.

13. The system of claim 9, comprising an additional wireless sensor configured to be disposed on a piston internal to the reciprocating internal combustion engine and to output an additional wireless signal to the controller indicative of a frequency of vibration of the piston.

14. A system, comprising:
 a wireless sensor disposed in a recess of a shank of a connecting rod internal to a reciprocating combustion engine and to communicate wirelessly; and
 a controller configured to execute computer instructions, comprising a processor, configured to:
  initiate communication with the wireless sensor disposed in the recess of the shank of the connecting rod internal to the reciprocating combustion engine by receiving a wireless signal from the wireless sensor, the wireless signal indicative of a frequency of vibration of the connecting rod;
  obtain an acceptable threshold range of vibrations for the connecting rod from one or more data sources;
  determine whether the frequency of vibration is within the acceptable threshold range of vibrations for the connecting rod; and
  initiate preventative actions when the frequency is not within the acceptable threshold range, wherein the preventative actions comprise controlling operation of the reciprocating combustion engine.

15. The system of claim 14, wherein initiating the one or more preventative actions comprises initiating sending of an alert to display on a user interface screen of a monitoring system, initiating sending of the alert to a workstation to display, or some combination thereof.

16. The system of claim 14, wherein obtaining the acceptable threshold range comprises obtaining the acceptable threshold range from local or remote data sources as the one or more data sources.

17. The system of claim 14, wherein obtaining the acceptable threshold range comprises retrieving pre-stored test data, a design specification, or some combination thereof, related to the connecting rod.

18. The system of claim 14, wherein the instructions are configured to determine that the connecting rod is cracked when frequencies of vibration exceed the acceptable threshold range of vibrations.

19. The system of claim 14, comprising an additional wireless sensor configured to be disposed on a piston internal to the reciprocating internal combustion engine and to output an additional wireless signal to the controller indicative of a frequency of vibration of the piston.

20. A system, comprising:
 a reciprocal combustion engine;

a wireless sensor disposed in a recess of a shank of a connecting rod internal to the reciprocating combustion engine, said wireless sensor configured to communicate wirelessly; and a controller comprising a processor configured to:
  initiate communication with the wireless sensor disposed in the recess of the shank of the connecting rod internal to the reciprocating combustion engine by receiving a wireless signal from the wireless sensor, the wireless signal indicative of a frequency of vibration of the connecting rod;
  obtain an acceptable threshold range of vibrations for the connecting rod from one or more data sources;
  determine whether the frequency of vibration is within the acceptable threshold range of vibrations for the connecting rod; and
  initiate preventative actions when the frequency is not within the acceptable threshold range, wherein the preventative actions comprise controlling operation of the reciprocating combustion engine.

21. The system of claim 20, wherein the processor is configured to wait for another wireless signal using a network interface, before initiating preventative actions, when the frequency is within the acceptable threshold range.

22. The system of claim 20, wherein the processor is configured to send an alert to display on a user interface screen of a control system, send the alert to a local or remote workstation to display, or some combination thereof, as the one or more preventative actions.

23. The system of claim 20, wherein the processor is configured to initiate communication with the wireless sensor by receiving a second wireless signal.

24. The system of claim 20, wherein the processor is configured to:
  initiate communication with the wireless sensor by receiving a wireless signal indicative of one or more angular velocity, acceleration, displacement, or some combination thereof, of the connecting rod from the wireless sensor;
  obtain an acceptable threshold range of angular velocity, acceleration, displacement, or some combination thereof, for the connecting rod from one or more data sources;
  determine whether the angular velocity, the acceleration, the displacement, or some combination thereof, is within the acceptable threshold range for the connecting rod; and
  initiate preventative actions when the angular velocity, the acceleration, the displacement, or some combination thereof, is not within the acceptable threshold range.

25. The system of claim 20, wherein the processor is configured to generate an indication that the connecting rod has cracked when the frequency of vibration exceeds the acceptable threshold range of vibration.

26. The system of claim 20, wherein the processor is configured to initiate waiting for another wireless signal using a network interface when the frequency is within the acceptable threshold range.

27. The system of claim 20, wherein the processor is configured to set a baseline value of the frequency of vibration when the wireless signal is initially received and to determine whether a phase of the frequency of vibration deviates from a phase of the baseline value for subsequently received wireless signals.

28. The system of claim 20, wherein initiating the one or more preventative actions comprises initiating sending of an alert to display on a user interface screen of a monitoring system, initiating sending of the alert to a workstation to display, or some combination thereof.

29. The system of claim 20, wherein obtaining the acceptable threshold range comprises obtaining the acceptable threshold range from local or remote data sources as the one or more data sources.

30. The system of claim 20, wherein obtaining the acceptable threshold range comprises retrieving pre-stored test data, a design specification, or some combination thereof, related to the connecting rod.

31. The system of claim 20, wherein the processor is configured to determine that the connecting rod is cracked when frequencies of vibration exceed the acceptable threshold range of vibrations.

32. The system of claim 20, wherein the acceptable threshold range of vibrations for the connecting rod is based at least in part on a natural frequency of the connecting rod.

33. The system of claim 20, wherein controlling operation of the reciprocating combustion engine comprises stopping the reciprocating combustion engine.

34. The system of claim 20, comprising an additional wireless sensor configured to be disposed on a piston internal to the reciprocating internal combustion engine and to output an additional wireless signal to the controller indicative of a frequency of vibration of the piston.

* * * * *